United States Patent
Lindström et al.

(10) Patent No.: US 6,577,703 B2
(45) Date of Patent: Jun. 10, 2003

(54) X-RAY MAMMOGRAPHY APPARATUS WITH A COMPRESSION PLATE THAT AUTOMATICALLY ADJUSTS TO UNIFORMLY APPLY PRESSURE

(75) Inventors: Krister Lindström, Älvsjö (SE); Helena Sundkvist, Bromma (SE); Eva Modig, Solna (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 10/007,488

(22) Filed: Nov. 5, 2001

(65) Prior Publication Data

US 2002/0061090 A1 May 23, 2002

(30) Foreign Application Priority Data

Nov. 23, 2000 (SE) ................................. 0004298

(51) Int. Cl.⁷ ................................................ A61B 6/04
(52) U.S. Cl. ........................................ 378/37; 378/208
(58) Field of Search ................................... 378/37, 208

(56) References Cited

U.S. PATENT DOCUMENTS

| | | | |
|---|---|---|---|
| 5,029,193 A | 7/1991 | Saffer | 378/37 |
| 5,506,877 A | 4/1996 | Niklason et al. | 378/37 |
| 5,706,327 A * | 1/1998 | Adamkowski et al. | 378/37 |
| 6,282,956 B1 * | 9/2001 | Okada | 73/504.12 |

FOREIGN PATENT DOCUMENTS

DE    299 08 202    10/1999

\* cited by examiner

*Primary Examiner*—Drew A. Dunn
*Assistant Examiner*—Courtney Thomas
(74) *Attorney, Agent, or Firm*—Schiff Hardin & Waite

(57) ABSTRACT

An X-ray diagnostics apparatus for mammography examinations has an arm for an X-ray tube and a subject table and a compression plate arranged between the X-ray tube and the subject table. The compression plate is connected via a mount to the arm and is displaceable along the arm. The compression plate is connected to the mount so that the compression plate is rotatable relative to the subject table in the longitudinal and transverse directions of the plate. The examination apparatus generates a pressure against the breast under examination that is automatically uniformly distributed over the breast in an optimum way, by connecting the compression plate to the mount with at least one resilient connecting element in at least one connecting point.

7 Claims, 5 Drawing Sheets

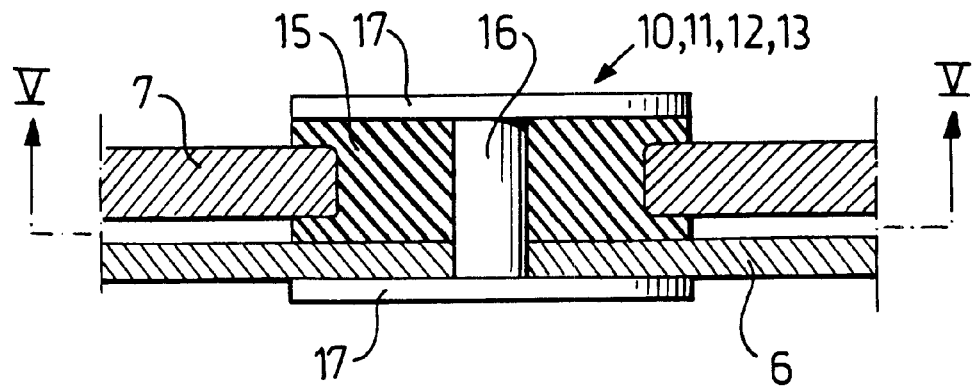
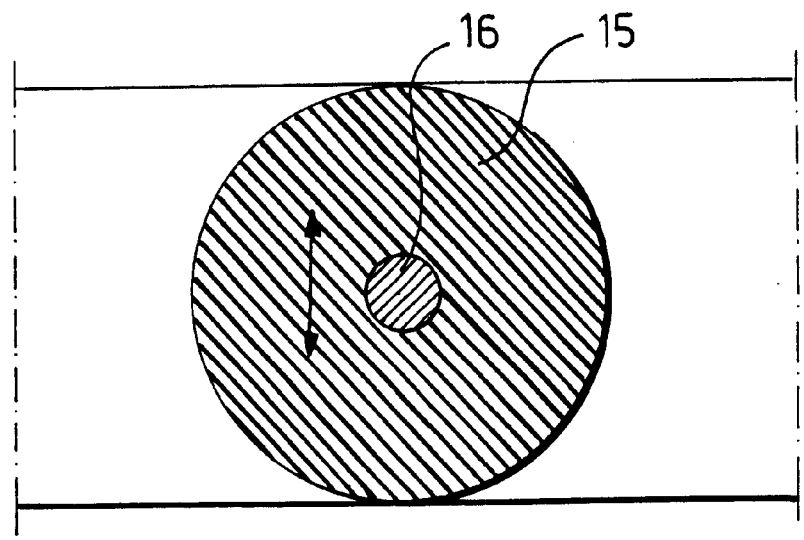

X-RAY MAMMOGRAPHY APPARATUS WITH A COMPRESSION PLATE THAT AUTOMATICALLY ADJUSTS TO UNIFORMLY APPLY PRESSURE

BACKGROUND OF THE INVENTION

1. Field of the Invention

The present invention is directed to an X-ray diagnostic apparatus for mammography examinations having an arm for an X-ray tube and a subject table and having a compression plate arranged between the X-ray tube and the subject table, the compression plate being connected via a mount to the arm and being displaceable along the arm, the compression plate being connected to the mount such that the compression plate is rotatable relative to the subject table in longitudinal and transverse directions of the plate.

2. Description of the Prior Art

In order to obtain the best possible image resolution of the breast with an optimally low X-ray dose in an exposure in a mammography examination, it is necessary that the compression plate be pressed against the breast under examination and lying against the subject table with a force that is uniformly distributed over the entire breast.

Since the breast is thicker close to the rib cage than at the nipple, an attempt has been made according to U.S. Pat. No. 5,706,327 to solve the problem of achieving uniform distribution of the compression force by rotatably connecting the compression plate to the mount such that the compression plate is rotatable relative to the subject table in the longitudinal direction thereof. This is achieved by the mount of the compression plate proceeding along a part of the two longitudinal sides of the compression plate, and by connecting the compression plate to the mount via shafts that are arranged respectively at the longitudinal sides. When the compression plate is pressed against the breast under examination, the compression plate is rotated around the shafts and therefore presses against both the portion proximate to the rib cage as well as against the portion at the nipple. A disadvantage of this structure is that the parts of the breast that are pressed laterally outwardly are not necessarily pressed together with the same compression force as the parts of the breast that are pressed together first by the compression plate.

An X-ray diagnostic apparatus of the type initially described is disclosed in U.S. Pat. No. 5,506,877. The mount of the compression plate is U-shaped and extends along the transverse side of the compression plate as well as along its two longitudinal sides. The compression plate is rotatably connected to the mount via shafts that are attached to the free ends of the mount. When, using known means, the compression plate and the mount are shifted toward the breast under examination, the compression plate is arranged parallel to the subject table. When the compression plate reaches the breast, it is rotated around the shafts in its longitudinal direction with means that are not described in U.S. Pat. No. 5,506,877 such that the compression plate presses both against the end proximate to the rib cage as well as against the nipple portion. The mount, and thus the compression plate as well, are motor-rotatable in the transverse direction around the center axis of the compression plate. As a result of this possibility of also being able to rotate the compression plate perpendicularly to the center axis, a uniformly distributed pressure over the entire breast can be obtained when the breast is correctly placed on the subject table. Placing the breast correctly means that the imaginary center axis of the breast should proceed along the center axis of the compression plate around which the plate is rotatable. A disadvantage of this known X-ray diagnostic apparatus is that all movements of the compression plate are driven with motors, which makes the apparatus expensive to manufacture.

SUMMARY OF THE INVENTION

An object of the present invention is to provide an X-ray examination apparatus for mammography examination of the type initially described having a compression plate that, using simple and thus comparatively inexpensive means, generates a pressure against the breast under examination that is automatically uniformly distributed over the breast in an optimum way.

This object is inventively achieved by connecting the compression plate to the holder with at least one resilient connecting element, at at least one connecting point. With the resilient connecting element, the compression plate—given a compression of a breast—can be automatically rotated in the longitudinal and transverse directions without the assistance of motors so that an optimum distribution of the force against the breast is achieved. As a result thereof, a high image resolution with a comparatively low X-ray dose is accomplished in an exposure.

In an extremely simple embodiment of the compression plate of the invention, a single connecting element is arranged in the middle of that side of the compression plate that is directed toward the mount. The aforementioned advantages are achieved as a result, particularly when the breast under examination is placed such that the imaginary center axis of the breast proceeds along or in the proximity of the center axis of the compression plate around which the plate is rotatable.

In a further embodiment of the compression plate of the invention, two connecting elements are arranged at respective sides of the middle of that side of the compression plate directed toward the mount. In addition to the advantages already mentioned, a further advantage is achieved in that the breast need not be brought into a special position relative to the compression plate. The compression plate has no defined rotational axis because the compression plate is connected to the mount in two resilient connecting points spaced from one another.

The mount can be fashioned U-shaped and proceed along one transverse side of the compression plate as well as along the two longitudinal sides thereof, with each longitudinal side of the compression plate being connected to the mount by at least one connecting element. The compression plate is connected to the mount in four points. The other two connecting elements are preferably attached to the transverse side of the compression plate, spaced from one another.

In another, embodiment of the compression plate of the invention, the mount is fashioned U-shaped and proceeds along the one transverse side of the compression plate as well as along both its longitudinal sides, with each longitudinal side of the compression plate connected to the mount with two connecting elements. The connecting elements are preferably arranged in the proximity of the corners of the compression plate. The number of resilient connecting elements and their placement in this embodiment of the compression plate is optimum in view of an automatic distribution of the pressure over the breast during a compression, regardless of where the breast has been placed on the subject table, since the compression plate has a flexible, non-defined rotational axis.

In another embodiment of the invention the mount is provided with at least one rubber bushing and the compression plate is connected to the rubber bushing via a shaft that is secured to the compression plate.

In a further embodiment of the invention the compression plate is provided with at least one rubber bushing and the mount is connected to the rubber bushing via a shaft that is secured to the mount. In conjunction with a compression, each shaft, given a rotation of the compression plate, is shifted in height in the longitudinal and transverse directions at each rubber bushing, so that a deformation of the respective rubber bushing ensues. After a compression ends, each rubber bushing automatically returns into its original shape.

DESCRIPTION OF THE DRAWINGS

FIG. 4 shows a resilient connecting element of the invention in a section along the section line IV—IV in FIG. 2

FIG. 5 shows a resilient connecting element along the section line V—V in FIG. 4.

DESCRIPTION OF THE PREFERRED EMBODIMENTS

Figure 1:
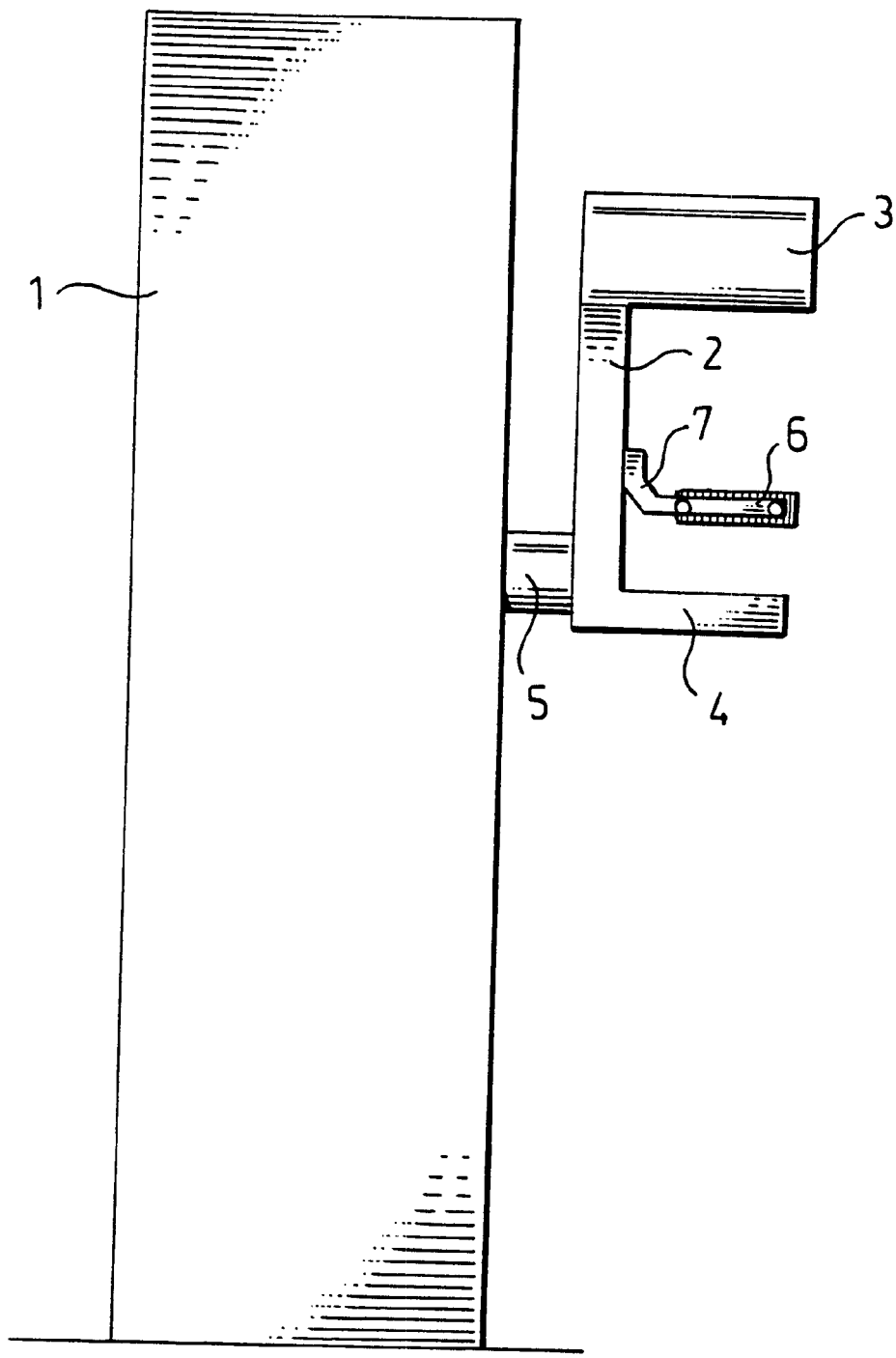
FIG. 1 is a side view of an X-ray diagnostic apparatus for mammography examinations having a mount and a compression plate of the invention.

FIG. 1 schematically shows an X-ray diagnostic apparatus for mammography examinations, having a stand 1 that carries an arm 2 for an X-ray tube 3 and a subject table 4. The arm 2 is rotatably connected to the stand 1 via a horizontally arranged shaft 5. A compression plate 6, which is connected to the arm 2 via a mount 7 and is displaceable along the arm 2, is arranged between the X-ray tube 3 and the subject table 4.

Figure 2:
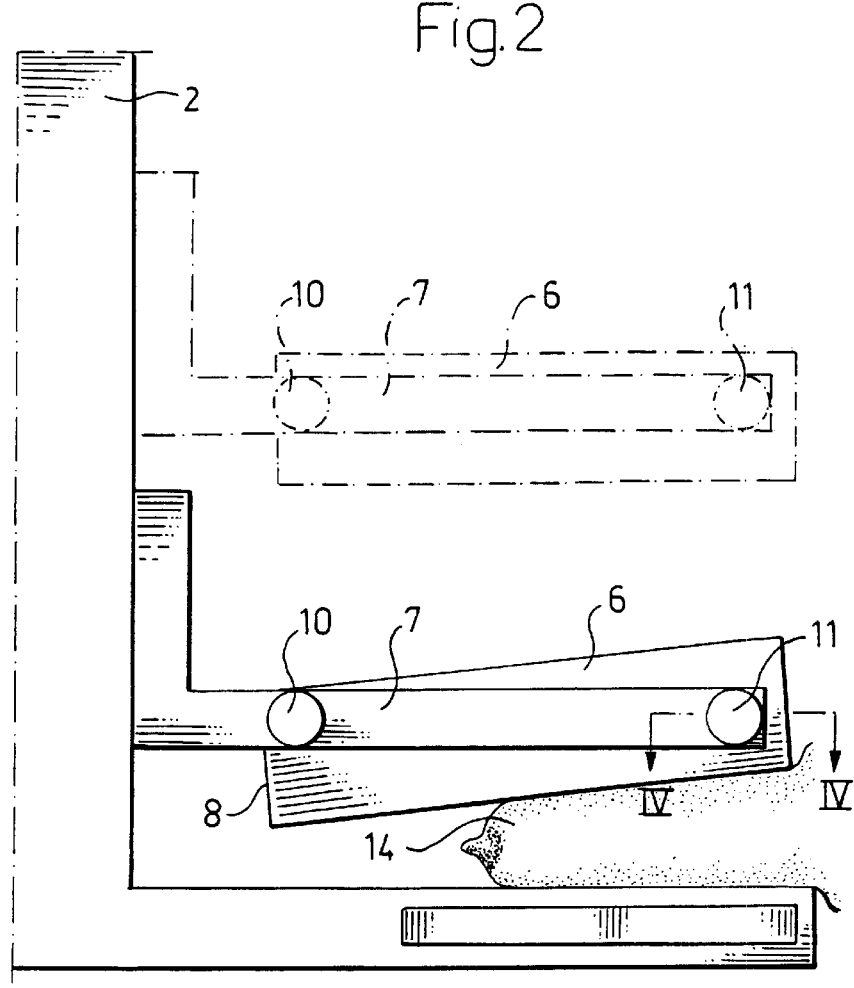
FIG. 2 is a side view of a mount and a compression plate of FIG. 1 in two different positions.
Figure 6:
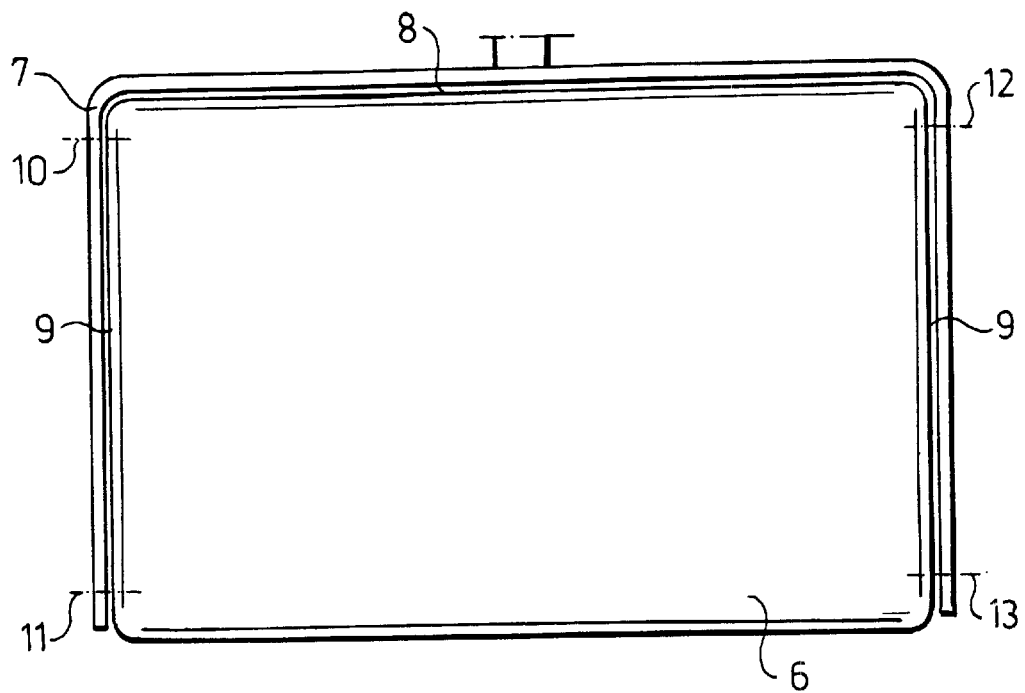
FIG. 6 is a plan view of a mount and a compression plate according to FIGS. 1 through 3 with schematically illustrated connecting elements.

FIG. 2 shows the mount 7 with the compression plate 6, the mount 7 being fashioned U-shaped and proceeding along the one transverse side 8 of the compression plate 6 as well as along both its longitudinal sides 9. Each longitudinal side 9 of the compression plate 6 is connected to the mount 7 with two resilient connecting elements 10 through 13. FIG. 6, which is a plan view of the mount 7 and the compression plate 6, shows an optimum placement of the connecting elements 10 through 13 arranged at the ends of each longitudinal side 9. In FIG. 6, the connecting elements 10 through 13 are only schematically shown. FIG. 2 shows the mount 7 and the compression plate 6 in a standby position. The dot-dash contours of the mount 7 and of the plate 6 show this position. In conjunction with an examination of a breast 14 that is on the subject table 3, the mount 7 and, as a result, the compression plate 6 as well are shifted along this arm 2. When the compression plate 6 has reached the end of the breast 14 proximate to the rib cage, this end is compressed, and the compression plate 6 rotates in its longitudinal direction due to the resilient connecting elements 10 through 13 so that the plate 6 compresses the entire breast 14 up to the nipple portion. The compression position of the plate 6 is shown in FIG. 2.

Figure 3:
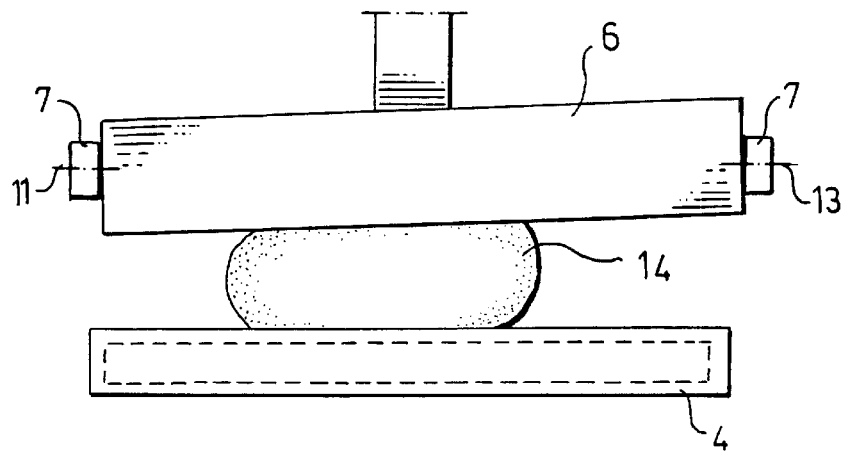
FIG. 3 is a front view of a mount and of a compression plate according to FIGS. 1 and 2.

As a result of the resilient connecting elements 10 through 13, the compression plate 6—as shown in FIG. 3—also can be rotated in relationship to the mount 7 in the transverse direction. Regardless of the placement of the breast 14 at the subject table 3, a uniformly distributed compressive pressure is obtained over the entire breast 14 due to the suspension of the compression plate 6 disclosed herein. This yields an extremely good image resolution in an exposure with an optimally low X-radiation dose.

FIG. 4 shows the resilient connecting elements 10 through 13. Each resilient connecting element 10 through 13 formed by a rubber bushing 15 that is firmly connected to the mount 7 and a shaft 16 that is firmly connected to the compression plate 6 and connects the compression plate 6 to the rubber bushing 15 and, thus, to the mount 7. The two ends of the shaft 16 are provided with cover disks 17.

FIG. 5, which shows a section along the section line V—V in FIG. 4, shows that the shaft 16 can be shifted such in the rubber bush 15 given a compression that the rubber bushing 15 is deformed. After a compression has been ended, the rubber bush 15 returns into its original shape.

Within the scope of the invention, the rubber bushing 15 also can be connected to the compression plate 6 and the shaft 16 can be connected to the mount 7.

Figure 7:
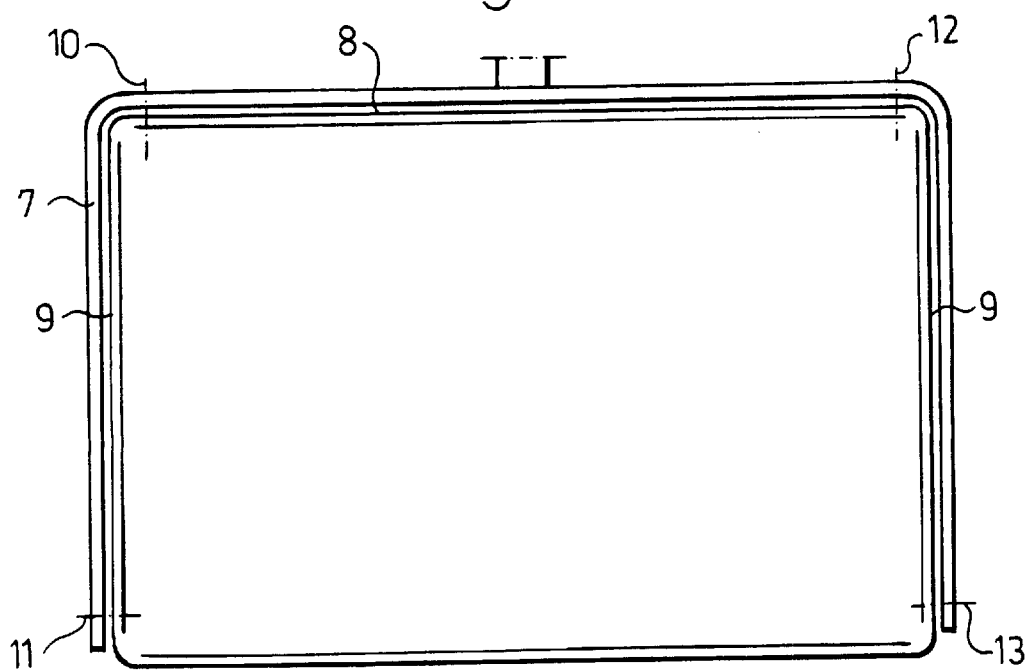
FIG. 7 is a plan view of a second embodiment of a mount and a compression plate of the invention with schematically illustrated connecting elements.

In a further exemplary embodiment, FIG. 7 shows that the resilient connecting elements 10 and 12 can be attached to the transverse side of the mount 7.

Figure 8:
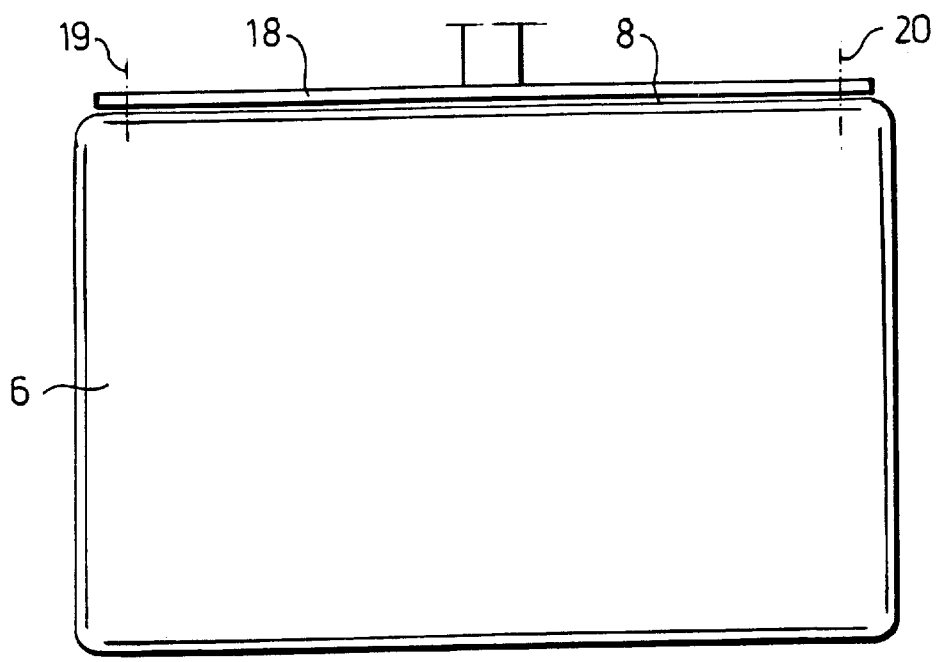
FIG. 8 is a plan view of a third embodiment of a mount and a compression plate of the invention with schematically shown connecting element.

FIG. 8 shows a mount 18 that extends only along the transverse side 8 of the compression plate 6, with resilient connecting elements 19, 20 being connected to the compression plate 6 in the region of the end sides of the mount 18.

Figure 9:
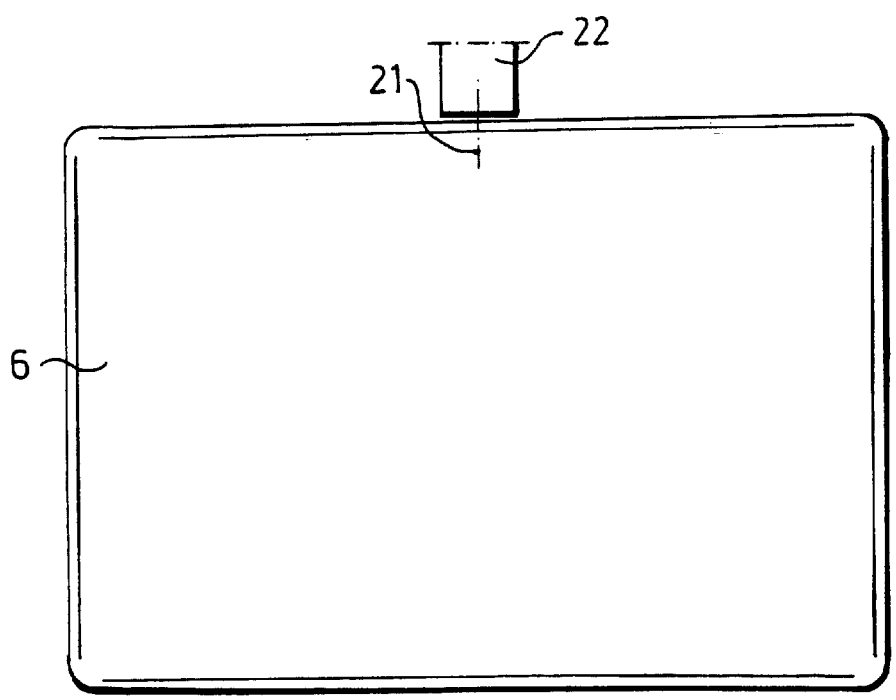
FIG. 9 is a plan view of a fourth embodiment of a mount and a compression plate of the invention with a schematically shown connecting elements.

FIG. 9 shows an especially simple embodiment of the invention wherein a single resilient connecting elements 21 is arranged in the middle of that side of the compression plate 6 that is directed toward the mount 22, i.e. in the middle of the transverse side 8.

With the assistance of a mount and of a compression plate as described, a uniform distribution of the force against the breast under examination can also be achieved by the exemplary embodiments of the invention shown in FIGS. 7 through 9.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray mammography apparatus comprising:

an X-ray tube;

a subject table adapted to receive a breast for examination;

an arm to which said X-ray tube and said subject table are attached;

a compression plate disposed between said X-ray tube and said subject table, and a mount connecting said compression plate to said arm allowing displacement of said compression plate toward and away from said subject table to apply a compression force to a breast on said subject table, said compression plate having a longitudinal direction and a transverse direction; and at least one resilient connector connecting said compression plate to said mount at at least one connecting location, said resilient connecting element allowing simultaneous non-driven rotation of said compression plate relative to said subject table in said longitudinal direction and in said transverse direction in response to compression of a breast between said compression plate and said subject table to uniformly distribute said compression force.

2. An X-ray mammography apparatus as claimed in claim 1 wherein said compression plate has a side facing toward said mount, and wherein said at least one resilient connecting element comprises a single connecting element disposed in a center of said side of said compression plate facing toward said mount.

3. An X-ray mammography apparatus as claimed in claim 1 wherein said compression plate has a side facing toward said mount, and wherein said at least one resilient connecting element comprises two resilient connecting elements respectively disposed at opposite sides of a center of said side of said compression plate facing toward said mount.

4. An X-ray mammography apparatus as claimed in claim 1 wherein said mount is U-shaped and proceeds along one transverse side of said compression plate and two longitudinal sides of said compression plate, and wherein said at least one resilient connecting element comprises two resilient connecting elements respectively connecting the longitudinal sides of the compression plate to said mount.

5. An X-ray mammography apparatus as claimed in claim 1 wherein said mount is U-shaped and proceeds along one transverse side of said compression plate and along both longitudinal sides of said compression plate, and wherein said at least one resilient connecting element comprises two resilient connecting elements respectively connecting each of said longitudinal sides of said compression plate to said mount.

6. An X-ray mammography apparatus as claimed in claim 1 wherein said at least one resilient connecting element comprises a rubber bushing to which said mount is attached, and a rigid shaft connected to said compression plate proceeding through said rubber bushing.

7. An X-ray mammography apparatus as claimed in claim 1 wherein said at least one resilient connecting element comprises a rubber bushing to which said compression plate is connected, and a rigid shaft connected to said mount and proceeding through said rubber bushing.

\* \* \* \* \*